US00PP25593P3

(12) United States Plant Patent
Lichacz

(10) Patent No.: US PP25,593 P3
(45) Date of Patent: May 26, 2015

(54) ***HOSTA* PLANT NAMED 'JUNE SPIRIT'**

(50) Latin Name: ***Hosta* hybrid (Tratt.)**
Varietal Denomination: June Spirit

(71) Applicant: Susan Lichacz, Zeeland, MI (US)

(72) Inventor: Susan Lichacz, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 253 days.

(21) Appl. No.: 13/986,091

(22) Filed: Mar. 29, 2013

(65) Prior Publication Data

US 2014/0298553 P1 Oct. 2, 2014

(51) Int. Cl.
*A01H 5/12* (2006.01)
*A01H 5/02* (2006.01)

(52) U.S. Cl.
CPC ..... *A01H 5/0272* (2013.01)
USPC ..... Plt./353

(58) Field of Classification Search
CPC ..... A01H 5/12; A01H 5/00; A01H 5/02
USPC ..... Plt./353
See application file for complete search history.

*Primary Examiner* — June Hwu

(57) ABSTRACT

*Hosta* plant named 'June Spirit' with cordate, heavy-substanced, shiny leaves having medium-wide deep-green margins and yellow-green centers. Flowers are medium lavender held attractively above the foliage on small-sized plant.

1 Drawing Sheet

Botanical classification: *Hosta* hybrid (Tratt.).
Variety denomination: 'June Spirit'.

BACKGROUND OF THE INVENTION

The present invention relates to the new and distinct *hosta* plant, *Hosta* 'June Spirit' discovered by Susan Lichacz at a nursery in Zeeland, Mich., USA on Jun. 18, 2008 as an uninduced whole plant mutation in a tissue cultured crop of *Hosta* 'June Fever' U.S. Plant Pat. No. 15,340. The new plant has been successfully asexually propagated both by division and by tissue culture at a nursery in Zeeland, Mich. and in both asexual propagation systems found to be stable and produce identical plants that maintain the unique characteristics of the original plant.

BRIEF SUMMARY OF THE INVENTION

*Hosta* 'June Spirit' differs from its mutation source parent, 'June Fever', as well as all other *hostas* known to the applicant. *Hosta* 'June Fever' is a mutation from *Hosta* 'Halcyon'. 'Halcyon' has produced multiple mutations and sports with green to blue-green margins and yellowish to cream centers including these similar but unique from 'June Spirit' include: 'Catherine' (not patented) and 'Katherine Lewis' (not patented), 'Ripple Effect' (not patented), 'Touch of Class' U.S. Plant Pat. No. 13,080, 'June' (not patented), 'Orange Star' U.S. Plant Pat. No. 22,384 and 'Remember Me' (not patented). *Hosta* 'June Spirit' is most similar to 'June Fever', 'Justine' U.S. Plant Pat. No. 21,624 and 'Orange Star' with all four having the shiny vernicose upper leaf surface, but the new plant has a much wider leaf margin and stiffer, more upright foliage than 'June Fever' and is faster growing than 'Justine' and 'Orange Star'. The leaf center of 'Orange Star' tends to be a lighter yellow than 'Justine' and 'June Spirit' under the same light intensity. All of the above have similar flower color.

'Catherine' and 'Touch of Class' appear to be indistinguishable from each other with a wide blue-green leaf margin, flat glaucous leaf and yellowish leaf center. 'Remember Me' has a bright creamy leaf center and blue-green margin with glaucous surface.

TABLE 1

| Cultivar | Margin color | Margin width | Center color | Leaf surface | Leaf structure |
|---|---|---|---|---|---|
| 'Halcyon' | blue-green | no variegation | blue-green | glaucous | flat |
| 'June' | blue-green | medium | yellow | glaucous | flat |
| 'June Fever' | green | thin | creamy-yellow | shiny | flat |
| 'June Spirit' | green | medium-wide | yellow-green | shiny | flat |
| Justine' | green | medium-wide | yellow-green | shiny | flat |
| Orange Star' | green | wide | yellow | shiny | flat |
| 'Remember Me' | blue-green | medium-thin | creamy | glaucous | flat |
| 'Touch of Class' | blue-green | wide | creamy-yellow | glaucous | flat |
| 'Catherine' | blue-green | medium | creamy-yellow | glaucous | flat |
| 'Katherine Lewis' | blue-green | medium | yellow-green | glaucous | flat |
| 'Ripple Effect' | blue-green | thin | creamy-yellow | glaucous | wavy |

There are over 4,900 cultivars registered with The American *Hosta* Society, which is the International Cultivar Registration Authority for the genus *Hosta* with another similar number of unregistered cultivars. *Hosta* 'June Spirit' differs from all these registered and unregistered cultivars known to the inventor in the following combined traits:

1. Plant of small size with upright to gradually arching foliage;
2. Cordate leaves with deep-green margins and yellow-green centers, shiny surface above and matte surface below;

3. Numerous flowers of medium lavender held attractively above foliage in mid-summer;

BRIEF DESCRIPTION OF THE DRAWINGS

The photographs of the three-year old plant demonstrate the overall appearance of the near-mature plant, including the unique traits, grown in a partially shaded garden in Zeeland, Mich. The colors are as accurate as reasonably possible with color reproductions. Ambient light spectrum, source, direction and temperature may cause the appearance of minor variation in color.

FIG. 1 shows a leaf close-up of a one-year old plant in the early part of the growing season.

DETAILED BOTANICAL DESCRIPTION

The following descriptions and color references are based on the 2001 edition of The Royal Horticultural Society Colour Chart except where common dictionary terms are used. The new plant, *Hosta* 'June Spirit', has not been observed under all possible environments. The phenotype may vary slightly with different environmental conditions, such as temperature, light, fertility, moisture and specimen maturity, but without any change in the genotype. The following observations and size descriptions are of a two-year old plant in a trial garden in Zeeland, Mich. with 50% artificial shade, supplemental water and light fertilizer.

Botanical classification: *Hosta* hybrid.

Mutation parentage: *Hosta* 'June Fever' U.S. Plant Pat. No. 15,340.

Propagation method: By sterile laboratory tissue culture propagation and garden division.

Growth rate: Moderate.

Crop time: Summer growing 10 to 12 weeks to finish in a one-liter container.

Time to initiate roots from tissue culture: About two and a half weeks.

Plant description:

*Plant shape and habit*.—Hardy, long-lived, herbaceous perennial, densely rhizomatous, forming a mounded clump in maturity, with basal rosette leaves; typically actinomorphic.

*Roots*.—Normal, fleshy, lightly branching, cream-colored in normal soil.

*Plant size*.—Foliage height about 26 cm tall; width of plant at the widest point is approximately 40 cm at the widest point just above soil line.

Foliage description:

*Leaf blade*.—Ovate; entire margins, cordate leaf base with acute apex, flat, mostly zygomorphic; without sinuous or pie-crust margins, with moderately impressed veins above; vernicose adaxial and matte abaxial; width to length ratio of about 1:1.7; average about 16.0 cm long and 9.5 cm wide; 10 to 11 pairs of major parallel veins on either side of one main center vein; glabrous; margin variegation portion increasing with age from ¼ to about ⅖ total leaf width.

*Blade color*.—Emerging and early season adaxial (top) center between RHS N144C and RHS N144B, adaxial margin between RHS 137A and RHS 136A, intermediate striated colors of RHS 138C, and nearest RHS N144D in small irregular patches between the margin and center where histogenic layers of the LI and LII do not evenly fold over each other; emerging and early season abaxial (bottom) center between RHS N144A and RHS 144A, abaxial margin nearest RHS 137A, intermediate colors of nearest RHS N144D and nearest RHS 144B in very small irregular patches between the margin and center; mid-season and later adaxial center between RHS 151D and RHS N144A in higher light and nearest RHS 151A in lower light intensity, mid-season and later adaxial margin between RHS 136A and RHS 137A and small irregular intermediate patches of nearest RHS 139C, nearest RHS N144C; mid-season and later abaxial center between RHS N144C and RHS 144B, and margins nearest RHS 136B and small irregular intermediate patches of nearest RHS N144D and nearest RHS 144B in very small irregular patches between the margin and center.

*Veins*.—10 to 11 pairs of major parallel veins, with one major center vein.

*Vein color*.—Adaxial center vein nearest RHS 145A; side adaxial veins same color as surrounding leaf tissue; abaxial center vein nearest RHS 145B and side veins same color as surrounding leaf tissue.

*Petioles*.—Concavo-convex, glabrous, glaucous, more upright toward the center of the clump to arching in the perimeter of the clump; 12 to 15 cm long and about 0.6 cm wide measured at 2.5 cm above soil line.

*Petiole color*.—Adaxial margins between RHS 136B and RHS 137B and adaxial centers nearest RHS 144B; abaxial margins between RHS 136B and RHS 137B and adaxial centers nearest RHS 144B.

Flower description:

*Buds*.—Clavate, acute to bluntly acute apex with longer thin base; one day prior to opening about 4.5 cm long, and 1.5 cm wide at the broadest portion.

*Bud color*.—Between RHS 91B and RHS 92B in distal region, lightening to lighter than RHS 91D in the mid-portion and then darkening to between RHS 76A and RHS 77D in the proximal region.

*Flowers*.—16 to 32 per scape closely aligned on the scape; each subtended by bract; perfect; funnelform; single; held mostly horizontal; about 4.0 cm wide and 7.5 cm long, (decreasing distally); remain open for a normal period, usually one to two days on or cut from plant; scapes remain effective from mid-July into early August in Zeeland, Mich.; no significant detectable fragrance.

*Tepals*.—Two sets of three fused at the basal two thirds; acute apex; margins entire; glabrous, approximately 6.5 cm long and 1.5 cm wide; with longitudinal lavender band about 7.0 mm wide with a white perimeter margin of about 3.5 mm wide.

*Tepal color*.—Two sets of tepals identical in color; abaxial tepal color between RHS 85D and RHS 85C on the center longitudinal band and lighter than RHS 85D on the margin with veins the same color as the surrounding tissue; adaxial tepal center longitudinal band more violet than RHS 77D and more purple than RHS 85A with three veins of nearest RHS 77B and a white margin of lighter than RHS N155D; all tepals have a thin vitreous margin of 1.0 to 1.5 mm wide.

*Pedicel*.—Cylindrical, slightly curved downward at time of flowering, matte, glabrous; about 10 mm long, 3 mm diameter; color nearest RHS 85C.

*Peduncle*.—Cylindrical, matte, glabrous, unbranched; usually one per division, slightly arching to about 80 degrees from horizontal; about 5 mm diameter at base, about 40 cm tall; color nearest RHS 138C with a slight tinting of RHS N187C.

*Gynoecium*.—Single. Style: about 6.5 cm long, protruding about 1.0 cm beyond tepals, 1 mm diameter, slightly curled upward at distal 1.0 cm; color nearest RHS 155 the whole length. Stigma: rounded, 1 mm to 2 mm in diameter, color lighter than RHS 155D. Ovary: ovoid with acute apex, about 6 mm long and 3 mm diameter; color between RHS 145A and RHS 145B.

*Androecium*.—Six. Filaments: six, about 1.0 mm in diameter and 5.5 cm long, shorter than gynoecium; with slight curve upward the proximal 1.0 mm; color lighter than RHS 11D throughout. Anthers: oblong; dorsifixed, versatile; dehiscing longitudinal; about 4 mm long and 1 mm wide; color nearest RHS N186B. Pollen: elliptical, less than 0.1 mm long, color between RHS 17B and RHS 17C.

*Bracts*.—Subtending individual or groups of two or three flowers, lanceolate, entire, vernicose, glabrous, concavo-convex, widest at middle and tapering to acute apex, sessile, clasping about ½ peduncle; about 1.5 cm long and 6.0 mm across before lowest flower, progressively decreasing in both length and width; drying as flowers open; protruding nearly perpendicular at time of flower opening.

*Bract color*.—Abaxial and adaxial 1.0 to 2.0 mm wide margins between RHS 137B and RHS 136B; central abaxial and adaxial portion between RHS 151A and RHS N144A with light tinting between RHS N187B and N186B.

*Fruit*.—Has not yet been observed.

*Seeds*.—Have not yet been observed.

Pest and disease resistance: Disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

I claim:

1. A new and distinct ornamental *Hosta* plant named 'June Spirit' as herein described and illustrated, suitable as a potted plant, for landscaping the garden, and for cut flower or leaf arrangements.

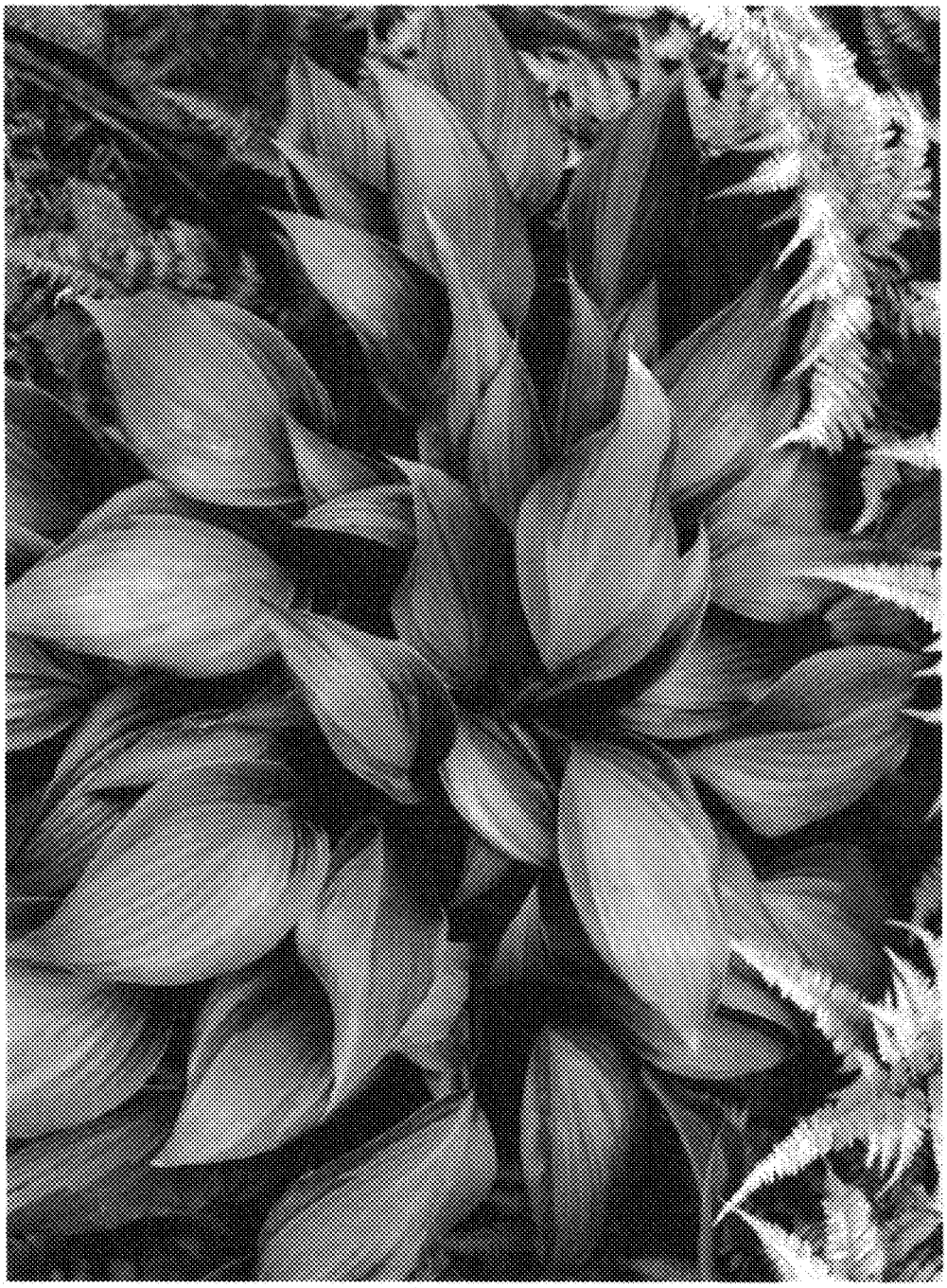

* * * * *